United States Patent
Li et al.

(10) Patent No.: US 11,944,599 B2
(45) Date of Patent: Apr. 2, 2024

(54) **METHOD OF EXTRACTING MYRICETIN FROM *XANTHOCERAS SORBIFOLIA BUNGE***

(71) Applicant: HEBEI RUILONG BIOTECHNOLOGY CO., LTD, Hebei (CN)

(72) Inventors: Weijia Li, Hebei (CN); Jingmei Zheng, Hebei (CN); Jingyi Yan, Hebei (CN); Junhua Wang, Hebei (CN)

(73) Assignee: HEBEI RUILONG BIOTECHNOLOGY CO., LTD, Shijiazhuang (CN)

( * ) Notice: Subject to any disclaimer, the term of this patent is extended or adjusted under 35 U.S.C. 154(b) by 0 days.

(21) Appl. No.: 18/478,522

(22) Filed: Sep. 29, 2023

(65) Prior Publication Data

US 2024/0075008 A1    Mar. 7, 2024

Related U.S. Application Data

(63) Continuation of application No. PCT/CN2023/102795, filed on Jun. 27, 2023.

(30) Foreign Application Priority Data

Aug. 31, 2022   (CN) .......................... 202211054260.8

(51) Int. Cl.
*A61K 31/352* (2006.01)
*A61K 36/77* (2006.01)

(52) U.S. Cl.
CPC ............ *A61K 31/352* (2013.01); *A61K 36/77* (2013.01); *A61K 2236/15* (2013.01); *A61K 2236/17* (2013.01); *A61K 2236/333* (2013.01); *A61K 2236/39* (2013.01); *A61K 2236/53* (2013.01)

(58) Field of Classification Search
None
See application file for complete search history.

(56) References Cited

U.S. PATENT DOCUMENTS

2022/0194915 A1    6/2022   Song et al.

FOREIGN PATENT DOCUMENTS

CN              113480508 A      10/2021

OTHER PUBLICATIONS

Yang et al.: "Chemical constituents from the stems of Xanthoceras sorbifolia", Chinese Traditional Patent Medicine, 2020, vol. 42, No. 8: pp. 2062-2066.
Liu et al.: "Research Progress on Plant Origins and Extraction Methods of Myricetin", Journal of Anhui Agricultural Sciences, 2014, vol. 42, No. 15: pp. 4781-4783, 4786.

*Primary Examiner* — Michael Barker
(74) *Attorney, Agent, or Firm* — Leason Ellis LLP

(57) ABSTRACT

A method of extracting myricetin from *Xanthoceras sorbifolia* Bunge is provided. The method includes: step 1, baking obtaining *Xanthoceras sorbifolia* Bunge crude powder; step 2, mixing the crude powder with a counter-current extraction solution to perform a counter-current extraction to obtain a filtrate and a filter residue; step 3, mixing the filter residue with a solvent to obtain a first mixture, and heating the first mixture to reflux for extraction to obtain an extraction liquid; step 4, mixing the extraction liquid and the filtrate, and concentrating under reduced pressure to obtain a concentrated solution; and step 5, separating and eluting the concentrated solution to obtain an eluent, then drying the eluent to obtain the myricetin.

6 Claims, No Drawings

METHOD OF EXTRACTING MYRICETIN FROM *XANTHOCERAS SORBIFOLIA* BUNGE

CROSS-REFERENCE TO RELATED APPLICATIONS

This application is a continuation of International Application No. PCT/CN2023/102795, filed on Jun. 27, 2023, which claims priority to Chinese Patent Application No. 202211054260.8, filed on Aug. 31, 2022. The disclosures of the aforementioned applications are hereby incorporated by reference in their entireties.

TECHNICAL FIELD

The disclosure relates to the technical field of extraction of an active ingredient from traditional Chinese medicine, and in particular to a method of extracting myricetin from *Xanthoceras sorbifolia* Bunge.

BACKGROUND

*Xanthoceras sorbifolia* Bunge is a member of the sapindaceae family and its wood, branches and leaves are used for medicinal purpose. It is mostly distributed in Northeast China, North China, Northwest China. It tastes slightly sweet, astringent and bitter, and has the effects of detumescence, pain relief and dampness elimination, which can be used clinically to treat rheumatoid arthritis, rheumatic internal fever, leprosy, etc. *Xanthoceras sorbifolia* Bunge contains flavonoids, coumarins and glycosides, where the flavonoids comprise dihydromyricetin, myricetin, quercetin, rutin, dihydroquercetin, xanthocerin and catechin.

Myricetin is a polyhydroxyflavonol compound, and easily soluble in methanol, ethanol, acetone, ethyl acetate and other organic solvents. When administered in a large dose, it has the effects of dampness elimination, relieving pain, and promoting blood circulation. At present, the method of preparing myricetin is mainly extracted from *Ampelopsis grossedentata* and *Ampelopsis* A.Rich. ex Michx. plants by a solvent. Since myricetin is prone to interference of other components during extraction, and in particular, interference of dihydromyricetin, resulting in low extraction rate and low purity, there is an urgent need to develop a method for extracting myricetin with high extraction rate and high purity.

SUMMARY

These and other problems are generally solved or circumvented, and technical advantages are generally achieved, by embodiments of the present disclosure which provide a method of extracting myricetin from *Xanthoceras sorbifolia* Bunge.

Technical Problems

The purpose of this application is to provide a method of extracting myricetin from *Xanthoceras sorbifolia* Bunge to solve the problems of low extraction rate and low purity of myricetin in the prior art.

Technical Solutions

This application adopts the following technical solution:
A method of extracting myricetin from *Xanthoceras sorbifolia* Bunge includes the following steps of step 1 to step 5.

Step 1, baking *Xanthoceras sorbifolia* Bunge, crushing the baked *Xanthoceras sorbifolia* Bunge, and sieving the crushed *Xanthoceras sorbifolia* Bunge to obtain a crude powder.

Step 2, mixing the crude powder with a counter-current extraction solution to perform a counter-current extraction at a low temperature to obtain a filtrate and a filter residue.

Step 3, mixing the filter residue with a solvent to obtain a first mixture, and heating the first mixture to reflux for extraction for 1 to 3 times to obtain an extraction liquid.

Step 4, mixing the extraction liquid obtained in step 3 and the filtrate obtained in step 2 to obtain a second mixture, adding an alkaline auxiliary agent to the second mixture to obtain a third mixture, and adjusting a pH of the third mixture to 8-9; heating to boil the third mixture after adjusting the pH to obtain a boiling mixture, reducing a temperature of the boiling mixture to room temperature, and concentrating under reduced pressure to obtain a concentrated solution.

Step 5, separating and eluting the concentrated solution with a monohydric alcohol aqueous solution in a macroporous adsorption resin to obtain an eluent, then drying the eluent to obtain the myricetin.

As an embodiment of the present application, in step 1, the *Xanthoceras sorbifolia* Bunge is baked at a temperature ranging from 80° C. to 100° C.

As an embodiment of the present application, in step 1, a water content of the crude powder is no greater than 2% (mass percent concentration).

As an embodiment of the present application, in step 2, a mass ratio of the crude powder to the counter-current extraction solution is 1:100 to 1:500.

As an embodiment of the present application, in step 2, the counter-current extraction solution includes sucrose ester, sulfonated castor oil and ethanol at a mass ratio of 4:1:500 to 4:1:1000.

As an embodiment of the present application, in step 2, the low temperature is 25° C. to 35° C., and the counter-current extraction is conducted for 20 minutes (min) to 40 min.

As an embodiment of the present application, in step 3, the solvent may comprise an alcohol, and/or acetone.

As an embodiment of the present application, in step 3, a mass ratio of the filter residue to the solvent is 1:5 to 1:20. When multiple extractions are performed in step 3, such as twice or three times, the mass ratio of the filter residue to the solvent in each extraction is 1:5 to 1:20.

As an embodiment of the present application, the alkaline auxiliary agent is saccharin sodium in step 4.

As an embodiment of the present application, in step 5, a volume percent concentration of the monohydric alcohol aqueous solution is 45% to 65%.

It is apparent to those skilled in the art that the counter-current extraction is a method of extracting active ingredients from a material to be extracted by continuous (or intermittent) counter-current contact of the material to be extracted and the extraction solution. In the present application, the material to be extracted is *Xanthoceras sorbifolia* Bunge. Before proceeding with a counter-current extraction, the *Xanthoceras sorbifolia* Bunge is firstly baked, crushed and sieved to obtain a crude powder; and then the crude powder is subjected to a counter-current extraction in an extraction solution to obtain the myricetin.

Advantageous Effects of the Disclosure

1. The present application adopts a counter-current extraction method at a low temperature, where a mixed solution of sucrose ester, sulfonated castor oil and ethanol is used as a counter-current extraction solution. In the counter-current extraction solution, the sucrose ester and the sulfonated castor oil are used in a compatibility manner, with a synergistic effect, such that the extracted myricetin has a high purity. Moreover, the counter-current extraction method at a low temperature disclosed in the present application makes a high extraction rate.

2. In the present application, dihydromyricetin is further converted into myricetin by adding the saccharin sodium during the extraction process of myricetin, thereby improving the extraction rate and purity of myricetin.

DETAILED DESCRIPTION OF ILLUSTRATIVE EMBODIMENTS

The technical solutions in the embodiments of the present application are clearly and completely described with reference to the embodiments of the present application in the following. Apparently, the embodiments to be described are merely a part rather than all of the embodiments of the present application. All other embodiments obtained by a person of ordinary skill in the art based on the embodiments of the present application without creative efforts shall belong to the scope of protection of the present application.

Embodiment 1

Step 1, 1 kilogram (kg) of *Xanthoceras sorbifolia* Bunge was baked at 80° C. until the water mass content was no greater than 2%, then the baked *Xanthoceras sorbifolia* Bunge was crushed and sieved to obtain a crude powder.

Step 2, the crude powder was mixed with the counter-current extraction solution to perform a counter-current extraction at 25° C. for 40 min to obtain a filtrate and a filter residue, a mass ratio of the crude powder to the counter-current extraction solution being 1:500, and the counter-current extraction solution included sucrose ester, sulfonated castor oil and ethanol at a mass ratio of 4:1:500.

Step 3, the filter residue was mixed with ethanol to obtain a first mixture, and the first mixture was heated to reflux for extraction for 1 time to obtain an extraction liquid, the mass ratio of the filter residue to the ethanol being 1:5.

Step 4, the extraction liquid obtained in step 3 was mixed with the filtrate obtained in step 2 to obtain a second mixture, saccharin sodium was added to the second mixture to obtain a third mixture, and the pH of the third mixture was adjusted to 8. The third mixture after adjusting pH was heated to boil to obtain a boiling mixture, then the temperature of the boiling mixture was reduced to room temperature. The mixture reduced to room temperature was concentrated under reduced pressure to obtain a concentrated solution.

Step 5, the concentrated solution was separated and eluted by aqueous ethanol solution with a volume percent concentration of 45% in a D101 macroporous adsorption resin to obtain an eluent, then the eluent was dried at 60° C. to obtain 6.8 grams (g) of myricetin.

Embodiment 2

Step 1, 1 kg of *Xanthoceras sorbifolia* Bunge was baked at 85° C. until the water mass content was no greater than 2%, then the baked *Xanthoceras sorbifolia* Bunge was crushed and sieved to obtain a crude powder.

Step 2, the crude powder was mixed with the counter-current extraction solution to perform a counter-current extraction at 30° C. for 30 min to obtain a filtrate and a filter residue, a mass ratio of the crude powder to the counter-current extraction solution being 1:300, and the counter-current extraction solution included sucrose ester, sulfonated castor oil and ethanol at a mass ratio of 4:1:700.

Step 3, the filter residue was mixed with ethanol to obtain a first mixture, and the first mixture was heated to reflux for extraction for 3 times to obtain an extraction liquid, the mass ratio of the filter residue to the ethanol in each extraction being 1:8.

Step 4, the extraction liquid obtained in step 3 was mixed with the filtrate obtained in step 2 to obtain a second mixture, saccharin sodium was added to the second mixture to obtain a third mixture, and the pH of the third mixture was adjusted to 9. The third mixture after adjusting pH was heated to boil to obtain a boiling mixture, then the temperature of the boiling mixture was reduced to room temperature. The mixture reduced to room temperature was concentrated under reduced pressure to obtain a concentrated solution.

Step 5, the concentrated solution was separated and eluted by aqueous ethanol solution with a volume percent concentration of 50% in a D101 macroporous adsorption resin to obtain an eluent, then the eluent was dried at 60° C. to obtain 6.6 grams of myricetin.

Embodiment 3

Step 1, 1 kg of *Xanthoceras sorbifolia* Bunge was baked at 90° C. until the water mass content was no greater than 2%, then the baked *Xanthoceras sorbifolia* Bunge was crushed and sieved to obtain a crude powder.

Step 2, the crude powder was mixed with the counter-current extraction solution to perform a counter-current extraction at 35° C. for 20 min to obtain a filtrate and a filter residue, a mass ratio of the crude powder to the counter-current extraction solution being 1:100, and the counter-current extraction solution included sucrose ester, sulfonated castor oil and ethanol at a mass ratio of 4:1:1000.

Step 3, the filter residue was mixed with methanol to obtain a first mixture, and the first mixture was heated to reflux for extraction for 2 times to obtain an extraction liquid, the mass ratio of the filter residue to the methanol in each extraction being 1:10.

Step 4, the extraction liquid obtained in step 3 was mixed with the filtrate obtained in step 2 to obtain a second mixture, saccharin sodium was added to the second mixture to obtain a third mixture, and the pH of the third mixture was adjusted to 8. The third mixture after adjusting pH was heated to boil to obtain a boiling mixture, then the temperature of the boiling mixture was reduced to room temperature. The mixture reduced to room temperature was concentrated under reduced pressure to obtain a concentrated solution.

Step 5, the concentrated solution was separated and eluted by aqueous methanol solution with a volume percent concentration of 60% in a D101 macroporous adsorption resin to obtain an eluent, then the eluent was dried at 60° C. to obtain 6.2 grams of myricetin.

Embodiment 4

Step 1, 1 kg of *Xanthoceras sorbifolia* Bunge was baked at 100° C. until the water mass content was no greater than 2%, then the baked *Xanthoceras sorbifolia* Bunge was crushed and sieved to obtain a crude powder.

Step 2, the crude powder was mixed with the counter-current extraction solution to perform a counter-current extraction at 30° C. for 40 min to obtain a filtrate and a filter residue, a mass ratio of the crude powder to the counter-current extraction solution being 1:400, and the counter-current extraction solution included sucrose ester, sulfonated castor oil and ethanol at a mass ratio of 4:1:900.

Step 3, the filter residue was mixed with acetone to obtain a first mixture, and the first mixture was heated to reflux for extraction for 3 times to obtain an extraction liquid, the mass ratio of the filter residue to the acetone in each extraction being 1:20.

Step 4, the extraction liquid obtained in step 3 was mixed with the filtrate obtained in step 2 to obtain a second mixture, saccharin sodium was added to the second mixture to obtain a third mixture, and the pH of the third mixture was adjusted to 8. The third mixture after adjusting pH was heated to boil to obtain a boiling mixture, then the temperature of the boiling mixture was reduced to room temperature. The mixture reduced to room temperature was concentrated under reduced pressure to obtain a concentrated solution.

Step 5, the concentrated solution was separated and eluted by aqueous methanol solution with a volume percent concentration of 65% in a D101 macroporous adsorption resin to obtain an eluent, then the eluent was dried at 60° C. to obtain 6.3 grams of myricetin.

Embodiment 5

Step 1, 1 kg of *Xanthoceras sorbifolia* Bunge was baked at 95° C. until the water mass content was no greater than 2%, then the baked *Xanthoceras sorbifolia* Bunge was crushed and sieved to obtain a crude powder.

Step 2, the crude powder was mixed with the counter-current extraction solution to perform a counter-current extraction at 35° C. for 40 min to obtain a filtrate and a filter residue, a mass ratio of the crude powder to the counter-current extraction solution being 1:350, and the counter-current extraction solution included sucrose ester, sulfonated castor oil and ethanol at a mass ratio of 4:1:750.

Step 3, the filter residue was mixed with acetone to obtain a first mixture, and the first mixture was heated to reflux for extraction for 1 time to obtain an extraction liquid, the mass ratio of the filter residue to the acetone being 1:18.

Step 4, the extraction liquid obtained in step 3 was mixed with the filtrate obtained in step 2 to obtain a second mixture, saccharin sodium was added to the second mixture to obtain a third mixture, and the pH of the third mixture was adjusted to 9. The third mixture after adjusting pH was heated to boil to obtain a boiling mixture, then the temperature of the boiling mixture was reduced to room temperature. The mixture reduced to room temperature was concentrated under reduced pressure to obtain a concentrated solution.

Step 5, the concentrated solution was separated and eluted by aqueous methanol solution with a volume percent concentration of 50% in a D101 macroporous adsorption resin to obtain an eluent, then the eluent was dried at 60° C. to obtain 6.5 grams of myricetin.

Comparative Embodiment 1

The difference from Embodiment 3 merely lied in that the counter-current extraction solution in step 2 in Comparative Embodiment 1 was ethanol, and the remaining steps and experimental parameters were the same as those in Embodiment 3. 4.3 grams of myricetin was obtained in Comparative Embodiment 1.

Comparative Embodiment 2

The difference from Embodiment 3 merely lied in that there was no sucrose ester in the counter-current extraction solution in step 2 in Comparative Embodiment 2, that is, the counter-current extraction solution in step 2 in Comparative Embodiment 2 included sulfonated castor oil and ethanol at a mass ratio of 1:1000. 4.9 grams of myricetin was obtained in Comparative Embodiment 2.

Comparative Embodiment 3

The difference from Embodiment 3 merely lied in that there was no sulfonated castor oil in the counter-current extraction solution in step 2 in Comparative Embodiment 3, that is, the counter-current extraction solution in step 2 in Comparative Embodiment 3 included sucrose ester and ethanol at a mass ratio of 4:1000. 5.1 grams of myricetin was obtained in Comparative Embodiment 3.

Comparative Embodiment 4

The difference from Embodiment 3 merely lied in that the alkaline auxiliary agent in step 4 in Comparative Embodiment 4 was an equal amount of sodium bicarbonate. 5.8 grams of myricetin was obtained in Comparative Embodiment 4.

Extraction rate (%)=(quality of myricetin/quality of *Xanthoceras sorbifolia* Bunge)×100%.

The purity of myricetin obtained in Embodiments 1 to 5 and Comparative Embodiments 1 to 4 was determined by high performance liquid chromatography (HPLC), and the experimental parameters of HPLC were conventional technical means in the art. The experiment results were shown in Table 1.

TABLE 1

| | | | | | | | | | |
|---|---|---|---|---|---|---|---|---|---|
| Extraction Rate and Purity of Myricetin. | | | | | | | | | |
| Item | Embodiment 1 | Embodiment 2 | Embodiment 3 | Embodiment 4 | Embodiment 5 | Comparative Embodiment 1 | Comparative Embodiment 2 | Comparative Embodiment 3 | Comparative Embodiment 4 |
| Extraction rate % | 0.68 | 0.66 | 0.62 | 0.63 | 0.65 | 0.43 | 0.49 | 0.51 | 0.58 |
| Purity (%) | 93.84 | 93.31 | 92.17 | 92.95 | 93.19 | 84.56 | 87.24 | 88.21 | 87.57 |

As can be seen from Table 1, the myricetin extracted from *Xanthoceras sorbifolia* Bunge in Embodiments 1 to 5 has a high extraction rate and purity.

In Comparative Embodiment 1, the counter-current extraction solution is ethanol that is a single component, in Comparative Embodiment 2, the counter-current extraction solution includes sulfonated castor oil and ethanol, and in Comparative Embodiment 3, the counter-current extraction solution includes sucrose ester and ethanol, all of which result in a poor extraction effect, and both the extraction rate and purity of myricetin are not as the Embodiments 1 to 5. After comparing the extraction rate and purity of myricetin in Comparative Embodiments 1 to 3 with those in Embodiment 3, it is found that both sucrose ester and sulfonated castor oil are in a compatibility manner and with a synergistic effect, which improves the extraction rate and purity of myricetin extracted from *Xanthoceras sorbifolia* Bunge.

The difference between Comparative Embodiment 4 and Embodiment 3 is only that the alkaline auxiliary agent in step 4 is replaced with an equal amount of sodium bicarbonate in Comparative Embodiment 4, resulting in a lower extraction rate and lower purity of myricetin in Comparative Embodiment 4 than those in Embodiment 3.

The above-mentioned embodiments are only used to illustrate the technical solutions of the disclosure, but not to limit the disclosure; although the present application has been described in detail with reference to the above-mentioned embodiments, those of ordinary skilled in the art should understand that: it is still possible to modify the technical solutions described in the above-mentioned embodiments, or to perform equivalent replacements for some of the technical features. However, these modifications or replacements do not make the essence of the corresponding technical solutions deviate from the spirit and scope of the technical solutions of the embodiments of the present application, and should be included within the protection scope of the present application.

What is claimed is:

1. A method of extracting myricetin from *Xanthoceras sorbifolia* Bunge, the method comprising:
   step 1, baking *Xanthoceras sorbifolia* Bunge, crushing the baked *Xanthoceras sorbifolia* Bunge, and sieving the crushed *Xanthoceras sorbifolia* Bunge to obtain a crude powder;
   step 2, mixing the crude powder with a counter-current extraction solution to perform a counter-current extraction at a low temperature to obtain a filtrate and a filter residue, a mass ratio of the crude powder to the counter-current extraction solution being 1:100 to 1:500, the counter-current extraction solution comprising sucrose ester, sulfonated castor oil and ethanol at a mass ratio of 4:1:500 to 4:1:1000, the low temperature being 25° C. to 35° C., wherein the counter-current extraction is conducted for 20 minutes (min) to 40 min;
   step 3, mixing the filter residue with a solvent to obtain a first mixture, and heating the first mixture to reflux for extraction for 1 to 3 times to obtain an extraction liquid;
   step 4, mixing the extraction liquid obtained in step 3 and the filtrate obtained in step 2 to obtain a second mixture, adding an alkaline auxiliary agent to the second mixture to obtain a third mixture, and adjusting a pH of the third mixture to 8-9; heating to boil the third mixture after adjusting the pH to obtain a boiling mixture, reducing a temperature of the boiling mixture to room temperature, and concentrating under reduced pressure to obtain a concentrated solution, the alkaline auxiliary agent being saccharin sodium; and
   step 5, separating and eluting the concentrated solution with a monohydric alcohol aqueous solution in a macroporous adsorption resin to obtain an eluent, then drying the eluent to obtain the myricetin.

2. The method of claim 1, wherein in step 1, the *Xanthoceras sorbifolia* Bunge is baked at a temperature ranging from 80° C. to 100° C.

3. The method of claim 1, wherein in step 1, a water content of the crude powder is no greater than 2%.

4. The method of claim 1, wherein in step 3, the solvent comprises an alcohol and/or acetone.

5. The method of claim 1, wherein in step 3, a mass ratio of the filter residue to the solvent is 1:5 to 1:20.

6. The method of claim 1, wherein in step 5, a volume percent concentration of the monohydric alcohol aqueous solution is 45% to 65%.

* * * * *